United States Patent
Ueda

(10) Patent No.: US 9,088,050 B2
(45) Date of Patent: Jul. 21, 2015

(54) ELECTRODE GROUP FOR THIN BATTERIES, THIN BATTERY, AND ELECTRONIC DEVICE

(75) Inventor: Tomohiro Ueda, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 218 days.

(21) Appl. No.: 13/880,901

(22) PCT Filed: Aug. 28, 2012

(86) PCT No.: PCT/JP2012/005403
§ 371 (c)(1),
(2), (4) Date: Apr. 22, 2013

(87) PCT Pub. No.: WO2013/031195
PCT Pub. Date: Mar. 7, 2013

(65) Prior Publication Data
US 2013/0260214 A1   Oct. 3, 2013

(30) Foreign Application Priority Data
Aug. 29, 2011 (JP) .................... 2011-185492

(51) Int. Cl.
*H01M 10/04* (2006.01)
*H01M 10/0585* (2010.01)
(Continued)

(52) U.S. Cl.
CPC ........... *H01M 10/0436* (2013.01); *A61N 1/303* (2013.01); *H01M 2/026* (2013.01);
(Continued)

(58) Field of Classification Search
CPC . H01M 10/585; H01M 10/0436; H01M 6/40; H01M 2/0207

USPC ......................................................... 429/162
See application file for complete search history.

(56) References Cited

U.S. PATENT DOCUMENTS 5,652,043 A   7/1997   Nitzan
5,811,204 A   9/1998   Nitzan
(Continued)

FOREIGN PATENT DOCUMENTS

CA   2306482 A1   2/1999
JP   9-161768 A   6/1997
(Continued)

OTHER PUBLICATIONS

International Search Report issued in International Patent Application No. PCT/JP2012/005403 mailed on Oct. 2, 2012.
(Continued)

*Primary Examiner* — Stewart Fraser
(74) *Attorney, Agent, or Firm* — McDermott Will & Emery LLP

(57) ABSTRACT

Provided is a high-capacity and highly-flexible electrode group for thin batteries, a thin battery including the electrode group, and an electronic device in which the thin battery is incorporated.
The electrode group for thin batteries includes: a sheet-like first electrode, a sheet-like second electrode being laminated on each of both surfaces of the first electrode, and an electrolyte layer interposed between the first electrode and the second electrode. The second electrode has a polarity opposite to that of the first electrode. The second electrode has a flexural modulus lower than that of the first electrode. The thin battery includes the electrode group, and a pouch-like housing accommodating the electrode group. The electronic device includes an electronic device main body with flexibility, and the thin battery is incorporated in the electronic device main body.

12 Claims, 7 Drawing Sheets

(51) Int. Cl.
*H01M 2/02* (2006.01)
*H01M 10/052* (2010.01)
*H01M 6/16* (2006.01)
*A61N 1/30* (2006.01)
*H01M 4/131* (2010.01)
*H01M 4/134* (2010.01)
*H01M 4/38* (2006.01)
*H01M 4/40* (2006.01)
*H01M 4/505* (2010.01)
*H01M 4/02* (2006.01)
*H01M 4/525* (2010.01)
*H01M 4/133* (2010.01)
*H01M 4/587* (2010.01)

(52) U.S. Cl.
CPC ............ *H01M 2/0275* (2013.01); *H01M 4/131* (2013.01); *H01M 4/134* (2013.01); *H01M 4/382* (2013.01); *H01M 4/405* (2013.01); *H01M 4/505* (2013.01); *H01M 6/16* (2013.01); *H01M 10/052* (2013.01); *H01M 10/0585* (2013.01); *H01M 4/133* (2013.01); *H01M 4/525* (2013.01); *H01M 4/587* (2013.01); *H01M 2004/021* (2013.01); *Y02E 60/122* (2013.01)

(56) References Cited

U.S. PATENT DOCUMENTS

| | | |
|---|---|---|
| 5,897,522 A | 4/1999 | Nitzan |
| 6,040,081 A | 3/2000 | Van Lerberghe |
| RE39,676 E | 6/2007 | Nitzan |
| 7,572,553 B2 | 8/2009 | Ohkubo et al. |
| 8,132,468 B2 * | 3/2012 | Radivojevic .................... 73/777 |
| 2004/0101763 A1 * | 5/2004 | Kotato et al. ................. 429/331 |
| 2006/0102455 A1 * | 5/2006 | Chiang et al. ................. 200/181 |
| 2008/0138702 A1 | 6/2008 | Nakamura et al. |
| 2013/0252065 A1 * | 9/2013 | Ueda ............................ 429/127 |

FOREIGN PATENT DOCUMENTS

| | | |
|---|---|---|
| JP | 10-064489 A | 3/1998 |
| JP | 10-189053 A | 7/1998 |
| JP | 11-345599 A | 12/1999 |
| JP | 2000-502206 A | 2/2000 |
| JP | 2000-348694 A | 12/2000 |
| JP | 2001-511592 A | 8/2001 |
| JP | 2002-504836 A | 2/2002 |
| JP | 2003-297374 A | 10/2003 |
| JP | 2008-071732 A | 3/2008 |
| JP | 2009-009897 A | 1/2009 |
| JP | 2011-258477 A | 12/2011 |
| WO | WO-97/22466 A1 | 6/1997 |
| WO | WO-98/56458 A1 | 12/1998 |
| WO | WO-99/05743 A1 | 2/1999 |

OTHER PUBLICATIONS

European Search Report dated Feb. 4, 2015 issued in the corresponding European Patent Application No. 12827657.3.

* cited by examiner (a)

(b)

(a)

(b)

ELECTRODE GROUP FOR THIN BATTERIES, THIN BATTERY, AND ELECTRONIC DEVICE

RELATED APPLICATIONS

This application is the U.S. National Phase under 35 U.S.C. §371 of International Application No. PCT/JP2012/005403, filed on Aug. 28, 2012, which in turn claims the benefit of Japanese Application No. 2011-185492, filed on Aug. 29, 2011, the disclosures of which Applications are incorporated by reference herein.

TECHNICAL FIELD

The present invention relates to an electrode group for thin batteries, a thin battery including the electrode group for thin batteries, and an electronic device in which the thin battery is incorporated.

BACKGROUND ART

In recent years, there has been advancement in small-size portable electronic devices such as cellular phones and hearing aids. Besides, devices that operate in contact with human body have been increasingly commercially available. For example, biological information measuring devices that acquire biological information such as body temperature, blood pressure, and pulse, and automatically transmit the acquired information to a facility such as a hospital have been developed. For another example, body-attached devices that, upon application of a potential to the skin of human body, supply medicine etc. through the skin into the body have been developed.

Under these circumstances, the batteries for supplying electric power to the above-mentioned small-size electronic devices are required to be thinner and more flexible. Thin batteries that have been already developed include paper batteries, thin flat batteries and plate-like batteries. In these batteries, the strength of the housing is high, but it is difficult to make the battery more flexible and further thinner.

In order to make the thin batteries more flexible and further thinner, a technique of using a thin and flexible laminated film as the housing has been proposed (see, e.g., Patent Literatures 1 and 2). Specifically, as shown in FIG. 9, a thin battery includes an electrode group 101 and a housing 102. The electrode group 101 is formed by stacking flat plate-like positive electrode and negative electrode with a separator interposed therebetween. A positive electrode lead 103 and a negative electrode lead 104 are electrically connected to the positive electrode and the negative electrode, respectively. The housing 102 is made of a laminated film, and serves to cover the positive and negative electrodes, while allowing the end portions of the positive and negative electrode leads to be exposed outside the housing. The exposed end portions are used as positive and negative electrode terminals.

Another possible technique for making thin batteries more flexible and further thinner is to reduce the thickness of the electrode group. For example, one proposal suggests forming an active material layer of the positive or negative electrode by a vapor phase process, thereby to reduce the thickness of the active material layer (see, e.g., Patent Literature 3).

CITATION LIST

Patent Literature

[PTL 1] Japanese Laid-Open Patent Publication No. Hei 11-345599
[PTL 2] Japanese Laid-Open Patent Publication No. 2008-71732
[PTL 3] Japanese Laid-Open Patent Publication No. 2009-9897

SUMMARY OF INVENTION

Technical Problem

In the conventional thin batteries, however, even though their housings are made of a laminated film, it is impossible to realize a necessary level of flexibility required for the batteries used in devices that operate in contact with human body, because the electrode groups are lacking in flexibility. The flexibility of the electrode group can be improved if the electrode group is made thinner by forming an active material layer using a vapor phase process. However, merely reducing the thickness of the active material layer in the conventional electrode group cannot provide a thin battery having a high capacity.

In view of the above, the present invention intends to provide a high-capacity and highly-flexible electrode group for thin batteries, a thin battery including such an electrode group, and an electronic device in which the thin battery is incorporated.

Solution to Problem

One aspect of the present invention is an electrode group for thin batteries including a sheet-like first electrode, a sheet-like second electrode laminated on each of both surfaces of the first electrode, and an electrolyte layer interposed between the first electrode and the second electrode. The second electrode has a polarity opposite to that of the first electrode. The flexural modulus of the second electrode is lower than that of the first electrode.

Another aspect of the present invention is a thin battery including the above battery group, and a pouch-like housing accommodating the electrode group. The sum of the thicknesses of the electrode group and the housing is 1.0 mm or less.

Yet another aspect of the present invention is an electronic device including an electronic device main body with flexibility, and the above thin battery. The thin battery is incorporated in the electronic device main body.

Advantageous Effects of Invention

According to the electrode group for thin batteries and the thin battery of the present invention, it is possible to achieve a high capacity and high flexibility. Moreover, according to the electronic device of the present invention, since high flexibility is achieved in the thin battery, the flexibility of the electronic device is not impaired. In addition, since a high capacity is achieved in the thin battery, the electronic device can be used for a long period of time, without the necessity of replacing or charging the battery.

While the novel features of the invention are set forth particularly in the appended claims, the invention, both as to organization and content, will be better understood and appreciated, along with other objects and features thereof, from the following detailed description taken in conjunction with the drawings.

DESCRIPTION OF EMBODIMENTS

Figure 1:
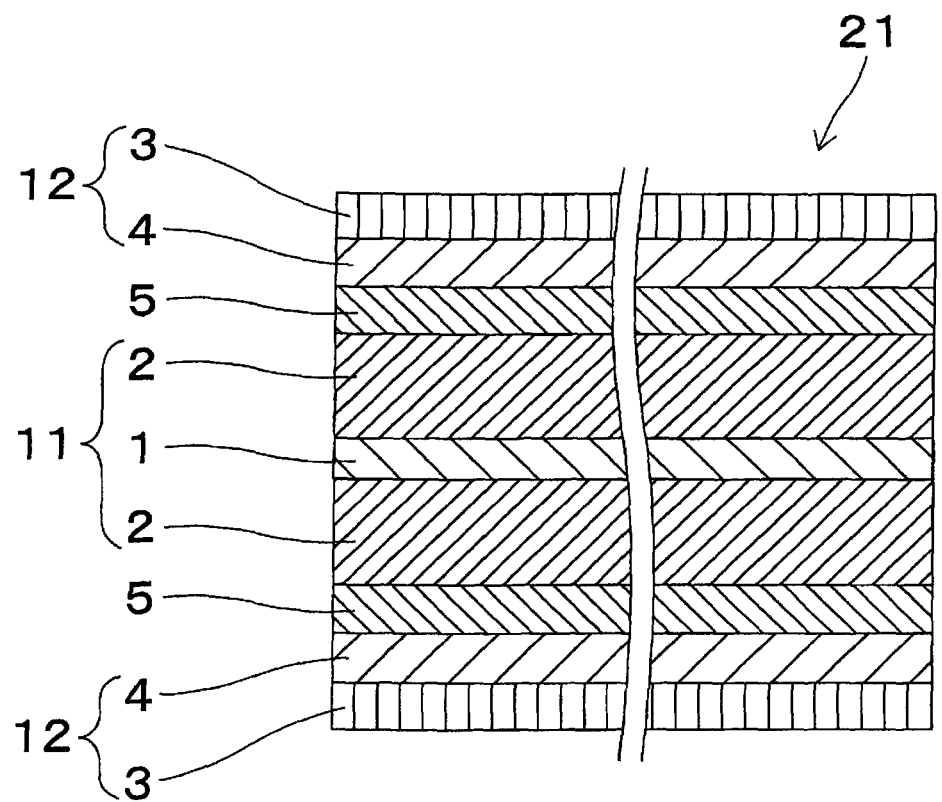
FIG. 1 A cross-sectional view schematically illustrating a configuration of an electrode group for thin batteries according to one embodiment of the present invention FIG. 2 A set of plane views of (a) a first electrode and (b) a second electrode included in the electrode group FIG. 3 A cross-sectional view schematically illustrating a configuration of a thin battery including the electrode group FIG. 4 A partially exploded oblique view of the thin battery FIG. 5 A set of (a) a front view and (b) a top view for explaining how to perform a three-point bending test FIG. 6 An illustration for explaining how to perform a flex resistance test for evaluation of flex-resistance reliability FIG. 7 An oblique view illustrating a biological information measuring device as an example of an electronic device including the thin battery FIG. 8 A cross-sectional view illustrating an iontophoresis-type transdermal administration device as another example of the electronic device including the thin battery FIG. 9 An exploded oblique view of a conventional thin battery FIG. 10 A diagram for explaining how force is applied to the electrode group when it is bent

The electrode group for thin batteries, the thin battery, and the electronic device of the present invention are described first.

The electrode group for thin batteries of the present invention includes a sheet-like first electrode, a sheet-like second electrode laminated on each of both surfaces of the first electrode, and an electrolyte layer interposed between the first electrode and the second electrode. The second electrode has a polarity opposite to that of the first electrode. The flexural modulus of the second electrode is lower than that of the first electrode.

In the above electrode group, the flexural modulus of the second electrode is lower than that of the first electrode. As such, the flexural modulus of the electrode group as a whole is low, and high flexibility can be achieved in the electrode group. Specifically, when the electrode group is bent, the upper and lower surfaces of the electrode group are stretched and compressed greatly. The stretch and compression at the center portion of the electrode group in its thickness direction, however, is small. Therefore, as in the above electrode group, by arranging the first electrode with high flexural modulus (i.e., low flexibility) at the center portion where the stretch and compression is small, and arranging the second electrode with low flexural modulus (i.e., high flexibility) at each of the upper and lower portions where the stretch and compression is great, the flexural modulus of the electrode group as a whole is reduced (the flexibility is improved).

In the above electrode group, the second electrode is laminated on each of both surfaces of the first electrode. An electrolyte layer is interposed between the first and second electrodes. As such, a high capacity can be achieved in the electrode group.

In order to achieve higher flexibility in the above electrode group, it is preferable to set the thickness of the electrode group to 700 μm or less, the flexural modulus of the first electrode to 100 MPa or more and 2000 MPa or less, and the flexural modulus of the second electrode to 20 MPa or more and 650 MPa or less.

Furthermore, in the above electrode group, the first electrode is preferably a positive electrode, and the second electrode is preferably a negative electrode. This is because in the case of selecting the constituent materials of the first and second electrodes such that the second electrode has a flexural modulus lower than that of the first electrode, the constituent materials can be more freely combined when the first electrode is a positive electrode and the second electrode is a negative electrode, than when the first electrode is a negative electrode and the second electrode is a positive electrode.

In a specific configuration of the above electrode group, the first electrode includes a positive electrode current collector, and a positive electrode active material layer formed on each of both surfaces of the positive electrode current collector. The second electrode includes a negative electrode current collector, and a negative electrode active material layer formed on one surface of the negative electrode current collector. The second electrode is formed on each of both surfaces of the first electrode such that the negative electrode active material layer faces the positive electrode active material layer. In this specific configuration, the positive electrode active material layer preferably includes manganese dioxide, and the negative electrode active material layer preferably includes lithium or a lithium alloy.

The thin battery of the present invention includes the above electrode group, and a pouch-like housing accommodating the electrode group. The sum of the thicknesses of the electrode group and the housing is 1.0 mm or less. Specifically, the housing is formed of a highly flexible film with excellent flex resistance. Therefore, in the thin battery also, high flexibility can be achieved. Using a highly flexible film with excellent flex resistance as the housing can improve the sealing reliability of the thin battery. This makes it possible to store the thin battery for a long period of time.

The electronic device of the present invention includes an electronic device main body with flexibility, and the above thin battery. The thin battery is incorporated in the electronic device main body. The electronic device is preferably a device that operates in contact with the skin of human body (a device with flexibility). The thin battery has high flexibility as described above. Therefore, the thin battery does not impair the flexibility of the electronic device. As such, the person who uses the device that operates in contact with human body is unlikely to feel discomfort even when the device is kept in close contact with the skin.

Next, embodiments of the present invention are specifically described below with reference to the drawings appended hereto.

FIG. 1 is a cross-sectional view schematically illustrating a configuration of an electrode group for thin batteries according to one embodiment of the present invention. As illustrated in FIG. 1, an electrode group 21 includes a first electrode 11, two second electrodes 12 having a polarity opposite to that of the first electrode 11, and two electrolyte layers 5. The first electrode 11 and the second electrodes 12 are sheet-like electrodes. The first electrode 11 has an electrode current collector 1, and electrode active material layers 2 formed on both surfaces of the electrode current collector 1 (the upper and lower surfaces thereof on the drawing sheet of FIG. 1). The second electrodes 12 each have an electrode current collector 3, and an electrode active material layer 4 formed on one surface of the electrode current collector 3.

The second electrodes 12 are laminated on both surfaces of the first electrode 11. Specifically, the second electrodes 12 are disposed one each on both sides of the first electrode 11 (the upper and lower sides thereof on the drawing sheet of FIG. 1) such that the electrode active material layer 4 faces the electrode active material layer 2. The electrolyte layers 5 are interposed one each between the first electrode 11 and the second electrodes 12.

In the electrode group 21, the constituent materials of the first and second electrodes 11 and 12 are selected such that the second electrode 12 has a flexural modulus lower than that of the first electrode 11. The details of the constituent materials are described later.

Figure 2:
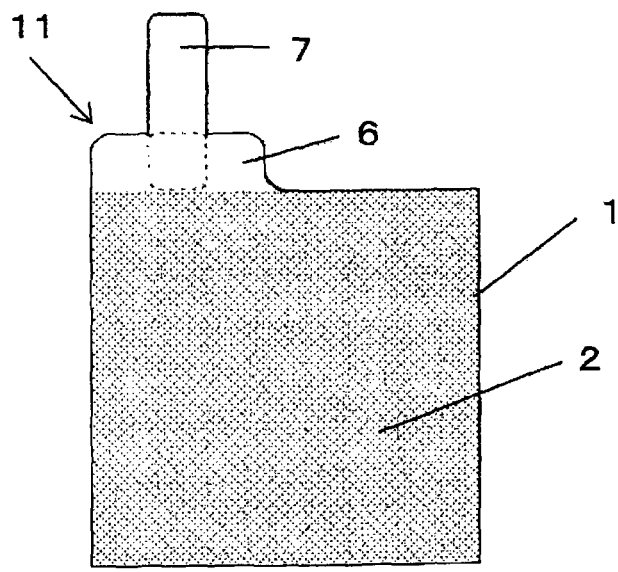
Figure 2:
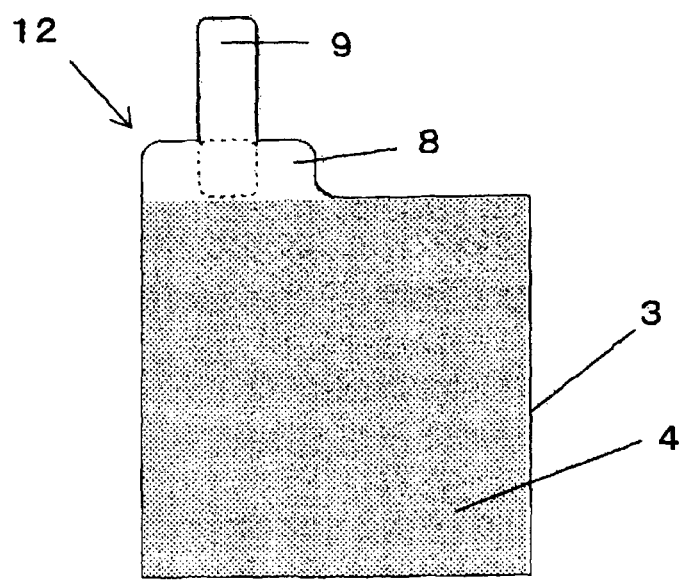

FIGS. 2(a) and 2(b) are plane views of the first and second electrodes, respectively. As illustrated in FIG. 2(a), the electrode current collector 1 of the first electrode 11 is provided with a protruding portion 6 extending outward from a part of the side thereof. An electrode lead 7 is electrically connected to the protruding portion 6. As illustrated in FIG. 2(b), the electrode current collector 3 of the second electrode 12 is provided with a protruding portion 8 extending outward from a part of the side thereof. An electrode lead 9 is electrically connected to the protruding portion 8. It is to be noted that the protruding portions 6 and 8 and the electrode leads 7 and 9 may be chamfered so that the corners thereof are rounded as illustrated in FIGS. 2(a) and 2(b). This can prevent the corners from getting snagged and damaging the protruding portions 6 and 8.

Figure 3:
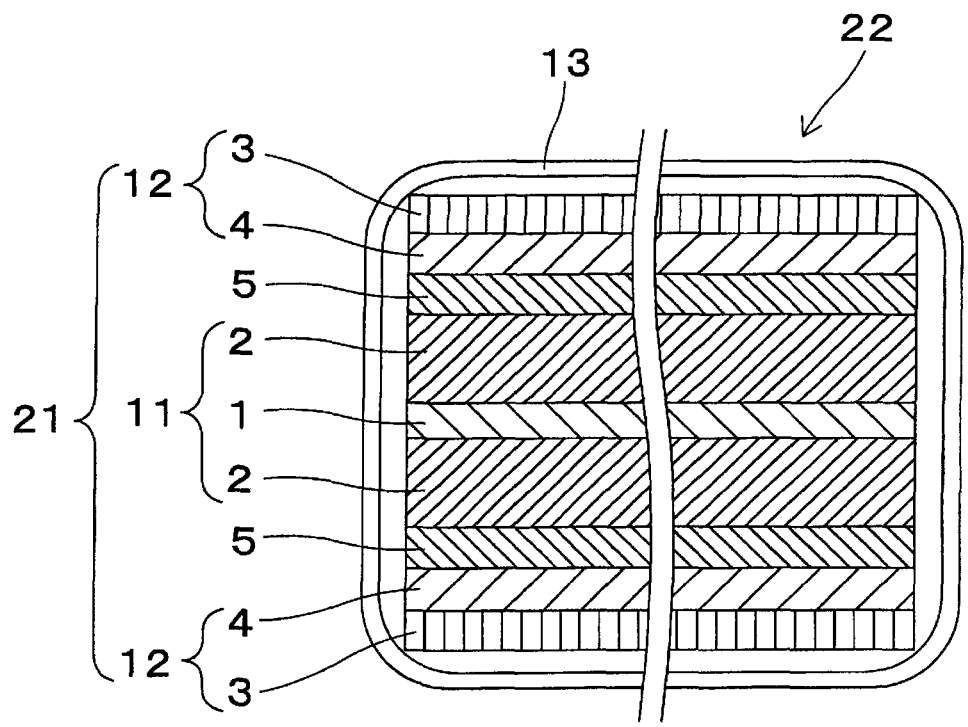
Figure 4:
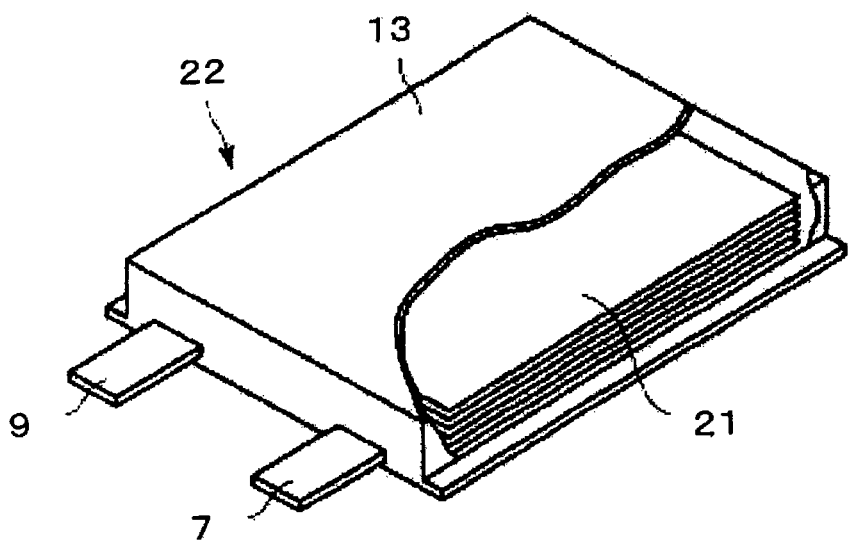

FIG. 3 is a cross-sectional view schematically illustrating a configuration of a thin battery including the above electrode group. FIG. 4 is a partially exploded oblique view of the thin battery. As illustrated in FIGS. 3 and 4, a thin battery 22 includes the electrode group 21, and a pouch-like housing 13 accommodating the electrode group 21. The electrode leads 7 and 9 are extended outside the housing 13, and are each partially exposed from the housing 13. The exposed portions of the electrode leads 7 and 9 function as electrode terminals. The thin battery 22 may be of flat-plate shape, or alternatively of curved-plate shape. The thin battery 22 may constitute a primary battery, or alternatively a secondary battery.

One of the first and second electrodes 11 and 12 is a positive electrode, and the other one of them is a negative electrode. In the configuration where the first electrode 11 is a positive electrode and the second electrode 12 is a negative electrode, the electrode current collector 1 is a positive electrode current collector, and the electrode active material layer 2 is a positive electrode active material layer. The electrode current collector 3 is a negative electrode current collector, and the electrode active material layer 4 is a negative electrode active material layer. Furthermore, the electrode lead 7 is a positive electrode lead, and the exposed portion of the electrode lead 7 serves as a positive electrode terminal. The electrode lead 9 is a negative electrode lead, and the exposed portion of the electrode lead 9 serves as a negative electrode terminal.

Conversely, in the configuration where the first electrode 11 is a negative electrode and the second electrode 12 is a positive electrode, the electrode current collector 1 is a negative electrode current collector, and the electrode active material layer 2 is a negative electrode active material layer. The electrode current collector 3 is a positive electrode current collector, and the electrode active material layer 4 is a positive electrode active material layer. Furthermore, the electrode lead 7 is a negative electrode lead, and the exposed portion of the electrode lead 7 serves as a negative electrode terminal. The electrode lead 9 is a positive electrode lead, and the exposed portion of the electrode lead 9 serves as a positive electrode terminal. It is to be noted, however, that the configuration where the first electrode 11 is a positive electrode and the second electrode 12 is a negative electrode is more preferable than this configuration. This is because in the case of selecting the constituent materials of the first and second electrodes 11 and 12 such that the second electrode 12 has a flexural modulus lower than that of the first electrode 11, the constituent materials can be more freely combined when the first electrode 11 is a positive electrode and the second electrode 12 is a negative electrode, than when the first electrode 11 is a negative electrode and the second electrode 12 is a positive electrode.

The positive electrode current collector may be made of a metal material such as metal film, metal foil, or non-woven fabric of metal fibers. Examples of the metal material include silver, nickel, palladium, gold, platinum, aluminum, and stainless steel. These may be used singly or in combination as the metal material for the positive electrode current collector. The thickness of the positive electrode current collector is, for example, 1 to 30 μm.

The positive electrode active material layer is a material mixture layer including a positive electrode active material and a binder. The positive electrode active material layer may further include a conductive agent, if necessary. Examples of the positive electrode active material include manganese dioxide, fluorinated carbons, sulfides, lithium-containing composite oxides, vanadium oxides and lithium compounds thereof, niobium oxides and lithium compounds thereof, conjugated polymers containing an organic conductive material, Chevrel-phase compounds, and olivine-type compounds. Preferred among them are manganese dioxide, fluorinated carbons, sulfides, and lithium-containing composite oxides, and particularly preferred is manganese dioxide. The thickness of the positive electrode active material layer is, for example, 10 to 200 μm.

Given that the reaction of manganese dioxide in the battery is a one-electron reaction, the theoretical capacity per mass of manganese dioxide is 308 mAh/g, which is a high capacity. In addition, manganese dioxide is inexpensive. A particularly preferred manganese dioxide is electrolytic manganese dioxide because it is easily available. Therefore, the positive electrode active material preferably contains manganese dioxide as its major component. It is to be noted that such a positive electrode active material may further contain a material other than manganese dioxide, such as a fluorinated carbon, vanadium oxide, or olivine-type compound. Moreover, manganese dioxide itself may contain a very small amount of impurities which unavoidably enter the manganese dioxide in the production process.

Examples of the fluorinated carbons include graphite fluoride represented by $(CF_w)_m$, where m is an integer of one or more, and $0<w\leq1$. Examples of the sulfides include $TiS_2$, $MoS_2$, and $FeS_2$. Examples of the lithium-containing composite oxides include $Li_{xa}CoO_2$, $Li_{xa}NiO_2$, $Li_{xa}MnO_2$, $Li_{xa}Co_yNi_{1-y}O_2$, $Li_{xa}Co_yM_{1-y}O_z$, $Li_{xa}Ni_{1-y}M_yO_z$, $Li_{xb}Mn_2O_4$, and $Li_{xb}Mn_{2-y}M_yO_4$. In the above formulae, M is at least one selected from the group consisting of Na, Mg, Sc, Y, Mn, Fe, Co, Ni, Cu, Zn, Al, Cr, Pb, Sb, and B; xa=0 to 1.2; xb=0 to 2.0; y=0 to 0.9; and z=2.0 to 2.3. Here, xa and xb are values before the start of charge and discharge, and increases and decreases during charge and discharge.

Examples of the conductive agent include: graphites such as natural graphite and artificial graphite; carbon blacks such as acetylene black, Ketjen black, channel black, furnace black, lamp black, and thermal black; conductive fibers such as carbon fiber and metallic fiber; metal powders, such as aluminum powder; conductive whiskers such as zinc oxide whisker and potassium titanate whisker; conductive metal oxides such as titanium oxide; and organic conductive materials such as phenylene derivative. These may be used singly or in combination as the conductive agent.

In view of improving the conductivity of the positive electrode active material layer and increasing the capacity of the positive electrode, the content of the conductive agent in the positive electrode active material layer is preferably 1.0 to 30 parts by mass per 100 parts by mass of the positive electrode active material.

Examples of the binder include polyvinylidene fluoride (PVDF), polytetrafluoroethylene, polyethylene, polypropylene, aramid resin, polyamide, polyimide, polyamide-imide, polyacrylonitrile, polyacrylic acid, polymethyl acrylate, polyethyl acrylate, polyhexyl acrylate, polymethacrylic acid, polymethyl methacrylate, polyethyl methacrylate, polyhexyl methacrylate, polyvinyl acetate, polyvinylpyrrolidone, polyether, polyether sulfone, hexafluoropolypropylene, styrene-butadiene rubber, and carboxymethyl cellulose. These may be used singly or in combination as the binder.

In view of improving the bonding property of the positive electrode active material layer and increasing the capacity of the positive electrode, the content of the binder in the positive electrode active material layer is preferably 1.0 to 15 parts by mass per 100 parts by mass of the positive electrode active material.

The binder may alternatively be a polymer electrolyte. The polymer electrolyte facilitates diffusion of lithium ions in the positive electrode active material layer. The polymer electrolyte may be used singly as the binder or in combination with another binder.

The negative electrode current collector may be an electrolytic metal foil obtained by electrolysis, or alternatively a rolled metal foil obtained by rolling. The electrolysis is advantageous in that it is excellent in mass-productivity of negative electrode current collectors, and thus can reduce the production cost of the negative electrode current collector. The rolling is advantageous in that it can easily reduce the thickness of the negative electrode current collector, and thus can reduce the weight of the negative electrode current collector. A rolled metal foil has excellent flex resistance because its crystals are oriented in the rolling direction. Therefore, a rolled metal foil can be suitably used for a thin flexible battery.

Examples of the constituent material of the negative electrode current collector include copper, a copper alloy, nickel, and stainless steel. The thickness of the negative electrode current collector is, for example, 1 to 50 µm.

The negative electrode active material is particularly preferably lithium or a lithium alloy (hereinafter referred to as a "lithium-based negative electrode") which is a high capacity active material. Examples of the lithium alloy include Li—Si alloy, Li—Sn alloy, Li—Al alloy, Li—Ga alloy, Li—Mg alloy, and Li—In alloy. In view of increasing the capacity of the negative electrode, the content of elements other than Li in the lithium alloy is preferably 0.1 to 10 mass %. The thickness of the negative electrode active material layer is, for example, 5 to 100 µm.

The negative electrode active material may be selected as appropriate from known materials and compositions. Using a lithium-based negative electrode, various natural and artificial graphites, silicides, silicon oxides, or various alloy materials can produce the thin battery 22 with high energy density. Among them, a lithium-based negative electrode is particularly preferred as the negative electrode active material because this can produce the thin battery 22 with high capacity and high energy density.

In forming a negative electrode, a negative electrode active material layer is allowed to adhere to a negative electrode current collector by a method such as press fitting, vapor deposition, or application. Thereafter, the negative electrode current collector is subjected to rolling or the like to bring the negative electrode current collector and the negative electrode active material layer into close contact with each other.

The constituent material of the electrolyte layer 5 is preferably a non-aqueous electrolyte that can provide a wide potential window. Example of such electrolyte include a dry polymer electrolyte in which an electrolyte salt is contained in a polymer matrix, a gel polymer electrolyte in which a solvent and an electrolyte salt are impregnated into a polymer matrix, an inorganic solid electrolyte, and a liquid electrolyte in which an electrolyte salt is dissolved in a solvent.

The dry polymer electrolyte comprises an electrolyte salt, and a polymer compound in which the electrolyte salt is dissolved. Examples of the polymer compound include ether polymers such as polyethylene oxide and cross-linked products thereof, polymethacrylate polymers, and polyacrylate polymers. These polymers may be used singly or used by being copolymerized or mixed.

The polymer matrix of the gel polymer electrolyte may be any polymer that is gelled upon absorbing liquid electrolyte. For example, the matrix polymer may be silicon gel, acrylic gel, acrylonitrile gel, a polyphosphazene-modified polymer, polyethylene oxide, polypropylene oxide, a fluorine-based polymer, or a composite, cross-linked or modified polymer of these. Examples of the fluorine-based polymer include: polymer materials such as polyvinylidene fluoride, vinylidene fluoride-hexafluoropropylene copolymer, vinylidene fluoride-trifluoroethylene copolymer, and vinylidene fluoride-tetrafluoroethylene copolymer; and mixtures of these. In view of improving the redox stability, the polymer matrix is preferably a fluorine-based polymer. The addition of an electrolyte salt to a gel polymer electrolyte renders the gel polymer electrolyte ionically conductive.

In the case where the constituent material of the electrolyte layer 5 is a dry polymer electrolyte or a gel polymer electrolyte, the leakage of electrolyte from the housing 13 can be prevented even when the housing 13 of the thin battery 22 is damaged. Furthermore, in the case where the constituent material of the electrolyte layer 5 is a dry polymer electrolyte or a gel polymer electrolyte, bending followability can be imparted to the electrolyte layer 5, i.e., when the thin battery 22 is bent, the electrolyte layer 5 can bend following the bending of the thin battery 22. Moreover, the adhesion within the electrode group 21 can be further improved. As such, even when the thin battery 22 is repetitively bent, the battery performance is unlikely to be varied or deteriorated. Therefore, the constituent material of the electrolyte layer 5 is preferably a dry polymer electrolyte or a gel polymer electrolyte.

To the dry polymer electrolyte and the gel polymer electrolyte, another component that does not impair the properties necessary for them to serve as the constituent materials of the electrolyte layer 5 may be added. Examples of such an additive include various inorganic fillers used for improving the strength, the homogeneity of the film, the ion conductivity, and the like. For example, fine particles such as alumina or silica fine particles can be used as the inorganic filler.

The constituent material of the electrolyte layer 5 may alternatively be an inorganic solid electrolyte. Examples of the inorganic solid electrolyte include: lithium halides such as lithium iodide, and derivatives thereof; lithium nitride; oxyacid salt-based materials; and sulfide-based materials.

The electrolyte layer 5 is formed by allowing an electrolyte such as a dry polymer electrolyte or a gel polymer electrolyte to be supported on a support. Various porous sheets known in the art may be used as the support. The porous sheet may be any porous sheet that can be used as a separator, such as a non-woven fabric of polypropylene, polyethylene, polyethylene terephthalate, cellulose, or polyphenylene sulfide; or a microporous film of polypropylene or polyethylene. By using a separator as the support, an electric short circuit between the first electrode 11 and the second electrode 12 can be prevented. For example, a porous sheet having a predetermined ion permeability, a predetermined mechanical strength, and a predetermined electrically insulating property may be used as the separator.

Alternatively, the electrolyte layer 5 may be formed by impregnating a separator with a liquid electrolyte. The liquid electrolyte is prepared by combining a non-aqueous solvent and an electrolyte salt, as appropriate. The non-aqueous solvent may be of any material that can be generally used for non-aqueous electrolyte batteries.

The housing 13 is preferably formed of a highly flexible film with excellent flex resistance. A preferable example of such a film is a film comprising a barrier layer and a resin layer formed on both surfaces or one surface of the barrier layer. In view of improving the strength and the flex resistance, the barrier layer is preferably made of aluminum, nickel, stainless steel, or an inorganic compound, and the thickness of the barrier layer is preferably 50 nm to 50 µm. The thickness of the resin layer is preferably 5 to 500 µm.

In view of improving the strength, the impact resistance, and the electrolyte resistance, it is preferable to form a resin layer (seal layer) on the inner side of the housing 13, thereby to reinforce the housing 13. The constituent material of such a resin layer is, for example, polyolefin such as polyethylene (PE) or polypropylene (PP), polyethylene terephthalate (PET), polyamide, polyurethane, or polyethylene-vinyl acetate copolymer material.

In view of improving the strength, the impact resistance, and the chemical resistance, it is preferable to form a resin layer (protective layer) on the outer side of the housing 13, thereby to protect the housing 13. The constituent material of such a resin layer is, for example, polyamide (PA) such as 6,6-nylon, PET, or polyolefin such as PE or PP.

Specifically, the housing 13 is formed of, for example, a modified-PP/PET/Al-layer/PET laminated film, a modified-PE/PA/Al-layer/PET laminated film, an ionomer-resin/Ni-layer/PE/PET laminated film, an ethylene vinyl acetate/PE/Al-layer/PET laminated film, an ionomer-resin/PET/Al-layer/PET laminated film, a PE/modified-PE/Al-layer/modified-PE/PE laminated film, or a PP/modified-PP/Al-layer/modified-PP/PP laminated film. The Al layer may be replaced with an inorganic compound layer such as $Al_2O_3$ layer or $SiO_2$ layer.

The electrode group 21 and the thin battery 22 according to the present embodiment can be produced, for example, in the manner as described below.

First, one first electrode 11 and two second electrodes 12 are prepared (see FIGS. 2(a) and 2(b)). The electrode leads 7 and 9 are electrically connected to the protruding portions 6 and 8, respectively. Thereafter, the second electrodes 12 are placed one each on both sides of the first electrode 11 such that the electrode active material layer 4 faces the electrode active material layer 2. The first electrode 11 and the second electrodes 12 are laminated with the electrolyte layers 5 interposed one each therebetween. In such a manner, the electrode group 21 as illustrated in FIG. 1 is formed. The protruding portions 8 may be electrically connected to each other by welding or riveting, and the electrode lead 9 may be electrically connected to only one of the protruding portions 8.

Next, a tubular film serving as the housing 13 is prepared. The electrode group 21 is inserted in the tubular film such that the electrode leads 7 and 9 are each partially exposed outside the tubular film through the opening thereof. Thereafter, the peripheral portion of the tubular film is fused in an atmosphere adjusted to have predetermined gas composition and pressure, thereby to seal the electrode group 21 in the tubular film. In such a manner, a thin battery as illustrated in FIG. 4 is fabricated. Here, the exposed portions of the electrode leads 7 and 9 constitute the electrode terminals of the thin battery 22.

Figure 10:
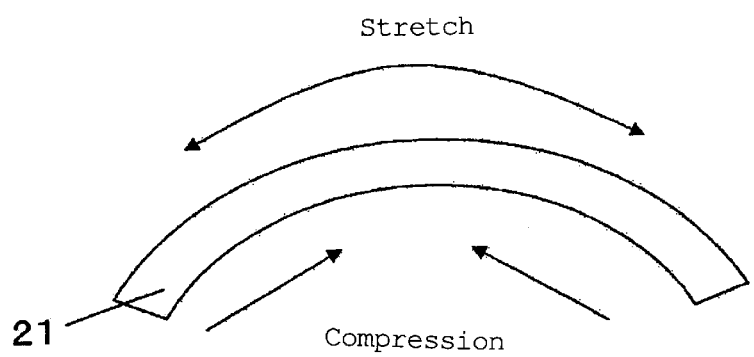

In the electrode group 21 according to the present embodiment, the flexural modulus of the second electrode 12 is lower than that of the first electrode 11. As such, the flexural modulus of the electrode group 21 as a whole is low, and high flexibility can be achieved in the electrode group 21. Specifically, as illustrated in FIG. 10, when the electrode group 21 is bent such that the upper surface thereof becomes convex, the upper surface is pulled and stretched, while the lower surface is pushed and compressed. In other words, the stretch and compression at the upper and lower surfaces of the electrode group 21 is great. On the other hand, the stretch and compression at the center portion of the electrode group 21 in its thickness direction is small. Therefore, as in the electrode group 21 of the present embodiment, by arranging the first electrode 11 with high flexural modulus (i.e., low flexibility) at the center portion where the stretch and compression is small, and arranging the second electrode 12 with low flexural modulus (i.e., high flexibility) at each of the upper and lower portions where the stretch and compression is great, the flexural modulus of the electrode group 21 as a whole is reduced (the flexibility is improved).

In the electrode group 21 according to the present embodiment, the second electrodes 12 are arranged one each on both surfaces of the first electrode 11. The electrolyte layers 5 are interposed one each between the first electrode 11 and the second electrodes 12. As such, a high capacity can be achieved in the electrode group 21.

In the thin battery 22 according to the present embodiment, the housing 13 is formed of a highly flexible film with excellent flex resistance. As such, high flexibility can be achieved also in the thin battery 22. Therefore, the thin battery 22 according to the present embodiment can be incorporated in an electronic device that requires the battery incorporated therein to be highly flexible (an electronic device with flexibility), such as a device that operates in contact with human body. In other words, the thin battery 22 does not reduce the flexibility of the electronic device. As such, when the thin battery 22 is incorporated in a device that operates in contact with human body, the person who uses the device feels almost no reduction in flexibility of the device, and therefore, is unlikely to feel discomfort.

By using a highly flexible film with excellent flex resistance as the housing 13, the sealing reliability of the thin battery 22 is improved. This makes it possible to store the thin battery 22 for a long period of time.

Moreover, the thin battery 22 includes the electrode group 21, and therefore, the thin battery 22 can also have a high capacity. As such, by incorporating the thin battery 22 in an electronic device, the electronic device can be used for a long period of time, without the necessity of replacing or charging the battery.

EXAMPLES

Examples of the present invention are specifically described below. It is to be noted, however, that these Examples described below are not to be construed as limiting the invention.

1. First Example

The electrode group 21 and the thin battery 22 were produced through the processes (1) to (5) as described below.

Here, the processes (1) and (5) were all carried out in a dry air atmosphere with a dew point of −30° C. or less.

(1) Preparation of First Electrode

Electrolytic manganese dioxide heated at 350° C., acetylene black serving as a conductive agent, and an N-methyl-2-pyrrolidone (NMP) solution (#8500, available from Kureha Corporation) containing polyvinylidene fluoride (PVDF) serving as a binder were mixed such that the ratio of manganese dioxide:acetylene black:PVDF was 100:5:5 by mass. To the resultant mixture, an appropriate amount of NMP was added, to prepare a paste of positive electrode material mixture.

The positive electrode material mixture was applied onto both surfaces of an aluminum foil (thickness: 20 μm) serving as a positive electrode current collector, and dried at 85° C. for 10 minutes, to form positive electrode active material layers on both surfaces of the aluminum foil. The aluminum foil was compressed at a linear pressure of 12,000 N/cm with a roll pressing machine. The thickness of each positive electrode active material layer was 90 μm.

Subsequently, the aluminum foil was punched out together with the positive electrode active material layers into a shape comprising a 50-mm×50-mm area and a 12-mm-wide×5-mm-long area protruding from said area (an area serving as the protruding portion 6), and then, dried at 120° C. for 2 hours under reduced pressure. In such a manner, the first electrode 11 was produced as a positive electrode. Thereafter, a 5-mm-wide×20-mm-long positive electrode lead made of aluminum (the electrode lead 7) was electrically connected to the protruding portion 6 by ultrasonic welding.

(2) Preparation of Second Electrode

A copper foil (thickness: 20 μm) serving as a negative electrode current collector was punched out into a shape comprising a 50-mm×50-mm area and a 12-mm-wide×5-mm-long area protruding from said area (an area serving as the protruding portion 8). Two copper foils having such a shape were prepared. A lithium metal foil (50 mm×50 mm, thickness: 20 μm) serving as a negative electrode active material was press-fitted to one surface (surface roughness: 2.6 μm) of each of the two copper foils at a linear pressure of 100 N/cm. In such a manner, two second electrodes 12 were produced as negative electrodes.

The protruding portions 8 were bonded to each other in an overlapping state by ultrasonic welding. Thereafter, a 3-mm-wide×20-mm-long negative electrode lead made of copper (the electrode lead 9) was electrically connected to one of the protruding portions 8 by ultrasonic welding.

(3) Formation of Electrolyte Layer

Propylene carbonate (PC) and dimethoxyethane (DME) were mixed in a ratio of PC:DME=6:4 (by mass), to prepare a non-aqueous solvent. To the non-aqueous solvent, lithium perchlorate (LiClO$_4$) was dissolved as an electrolyte salt at a concentration of 1 mol/kg, to prepare a liquid electrolyte.

Next, a copolymer of hexafluoropropylene and vinylidene fluoride (content of hexafluoropropylene: 7%) was prepared as a polymer matrix. The polymer matrix and dimethyl carbonate (DMC) were mixed in a ratio of polymer matrix:DMC=5:95 (by mass), to prepare a solution of polymer matrix.

The resultant solution of polymer matrix was uniformly applied onto both surfaces of a separator made of porous polyethylene and the surface of each positive electrode active material layer, and then, the solvent was volatilized. By doing this, the polymer matrix was applied onto the separator and the positive electrode active material layers.

(4) Fabrication of Electrode Group for Thin Batteries

The second electrodes 12 were stacked on both surfaces of the first electrode 11. Specifically, the second electrodes 12 were arranged one each on both sides of the first electrode 11 such that the negative electrode active material layer faced the positive electrode active material layer. The separator (thickness: 35 μm) with the polymer matrix applied thereto was interposed between the first electrode 11 and each second electrode 12. The resultant stack was hot pressed at 90° C. under 0.5 MPa for 1 minute, to form the electrode group 21 having a thickness of 350 μm (electrode group No. 1).

(5) Fabrication of Thin Battery

A tubular film (thickness: 70 μm) comprising an aluminum foil serving as a barrier layer, a polyethylene layer serving as a seal layer, and a polyethylene layer serving as a protective layer was prepared. Separately, propylene carbonate (PC) and dimethoxyethane (DME) were mixed in a ratio of PC:DME=6:4 (by mass), to prepare a non-aqueous solvent. To the resultant non-aqueous solvent, lithium perchlorate (LiClO$_4$) was dissolved as an electrolyte salt at a concentration of 1 mol/kg, to prepare a liquid electrolyte. The electrode group 21 was inserted in the tubular film such that the electrode leads 7 and 9 were each partially exposed outside through the opening of the tubular film, and the liquid electrolyte was injected into the tubular film through the opening thereof. The peripheral portion of the tubular film was fused (width of fused portion: 3 mm) in an atmosphere having a pressure of 660 mmHg, thereby to seal the electrode group 21 in the tubular film. In such a manner, the thin battery 22 of 60 mm wide×65 mm long×490 μm thick (battery No. 11) was produced.

2. First Comparative Example

In the first Comparative Example, in the process (1), a copper foil (thickness: 20 μm) serving as a negative electrode current collector was punched out into a shape comprising a 50-mm×50-mm area and a 12-mm-wide×5-mm-long area protruding from said area (an area serving as the protruding portion 6). A lithium metal foil (50 mm×50 mm, thickness: 20 μm) serving as a negative electrode active material was press-fitted to each of both surfaces (surface roughness: 2.6 μm) of the copper foil at a linear pressure of 100 N/cm. In such a manner, the first electrode 11 was produced as a negative electrode. Thereafter, a 3-mm-wide×20-mm-long negative electrode lead made of copper (the electrode lead 7) was electrically connected to the protruding portion 6 by ultrasonic welding.

In the process (2), two aluminum foils (thickness: 20 μm each) were prepared as positive electrode current collectors. The same positive electrode material mixture as that described in the first Example was applied onto one surface of each aluminum foil. The positive electrode material mixture was dried at 85° C. for 10 minutes, to form a positive electrode active material layer on each aluminum foil. Each aluminum foil was compressed at a linear pressure of 12,000 N/cm with a roll pressing machine. The thickness of the positive electrode active material layer of each aluminum foil was 90 μm.

Subsequently, each aluminum foil was punched out together with the positive electrode active material layer into a shape comprising a 50-mm×50-mm area and a 12-mm-wide×5-mm-long area protruding from said area (an area serving as the protruding portion 8). At this time, these aluminum foils were punched out such that the shapes of the two aluminum foils as seen from the positive electrode active material layer side were left-right symmetrical to each other. The resultant aluminum foils were dried at 120° C. for 2 hours under reduced pressure. In such a manner, two second electrodes 12 were produced as positive electrodes.

The protruding portions 8 were bonded to each other in an overlapping state by ultrasonic welding. Thereafter, a 3-mm-wide×20-mm-long positive electrode lead made of aluminum (the electrode lead 9) was electrically connected to one of the protruding portions 8 by ultrasonic welding.

Subsequently, the processes (3) to (5) were performed in the same manner as in the first Example, to form an electrode group (electrode group No. 101) and a thin battery (battery No. 111) according to the first Comparative Example.

3. Second Comparative Example

In the second Comparative Example, in the process (1), the same positive electrode material mixture as that described in the first Example was applied onto one surface of an aluminum foil (thickness: 20 μm) serving as a positive electrode current collector. The positive electrode material mixture was then dried at 85° C. for 10 minutes, to form a positive electrode active material layer on one surface of the aluminum foil. Next, the aluminum foil was compressed at a linear pressure of 12,000 N/cm with a roll pressing machine. The thickness of the positive electrode active material layer was 225 μm.

Subsequently, the aluminum foil was punched out together with the positive electrode active material layer into a shape comprising a 50-mm×50-mm area and a 12-mm-wide×5-mm-long area protruding from said area (an area serving as the protruding portion 6), and then dried at 120° C. for 2 hours under reduced pressure. In such a manner, the first electrode 11 was produced as a positive electrode. Thereafter, a 3-mm-wide×20-mm-long positive electrode lead made of aluminum (the electrode lead 7) was electrically connected to the protruding portion 6 by ultrasonic welding.

In the process (2), a copper foil (thickness: 20 μm) serving as a negative electrode current collector was punched out into a shape comprising a 50-mm×50-mm area and a 12-mm-wide×5-mm-long area protruding from said area (an area serving as the protruding portion 8). A lithium metal foil (50 mm×50 mm, thickness: 20 μm) serving as a negative electrode active material was press-fitted to one surface (surface roughness: 2.6 μm) of the copper foil at a linear pressure of 100 N/cm. In such a manner, the second electrode 12 was produced as a negative electrode. Thereafter, a 3-mm-wide×20-mm-long negative electrode lead made of copper (the electrode lead 9) was electrically connected to the protruding portion 8 by ultrasonic welding.

The process (3) was performed in the same manner as in the first Example. In the process (4), the second electrode 12 was stacked on one surface of the first electrode 11. Specifically, the second electrode 12 was arranged on one side of the first electrode 11 such that the negative electrode active material layer faced the positive electrode active material layer. At this time, the separator (thickness: 35 μm) with the polymer matrix applied thereto was interposed between the first electrode 11 and the second electrode 12. The resultant stack was hot pressed at 90° C. under 0.5 MPa for 1 minute, to form an electrode group according to the second Comparative Example (electrode group No. 102). The thickness of the electrode group 21 was 350 μm. The process (5) was performed in the same manner as in the first Example, to form a thin battery according to the second Comparative Example (battery No. 112).

4. Evaluation of Flexibility (Three-Point Bending Test)

The first and second electrodes, the electrode groups (electrode groups Nos. 1, 101 and 102), and the thin batteries (batteries Nos. 11, 111 and 112) according to the first Example, and the first and second Comparative Examples were subjected to a three-point bending test, using a Tensilon universal tester (RTC-1150A, available from Orientec Co., Ltd.), to measure a flexural modulus. The measurement of a flexural modulus was carried out in accordance with the method stipulated in JIS K7171. The measurement results of the flexural modulus were used to evaluate the flexibility. Here, the flexural modulus can serve as an index for evaluating the flexibility. To be specific, the lower the flexural modulus is, the higher the flexibility is.

Figure 5:
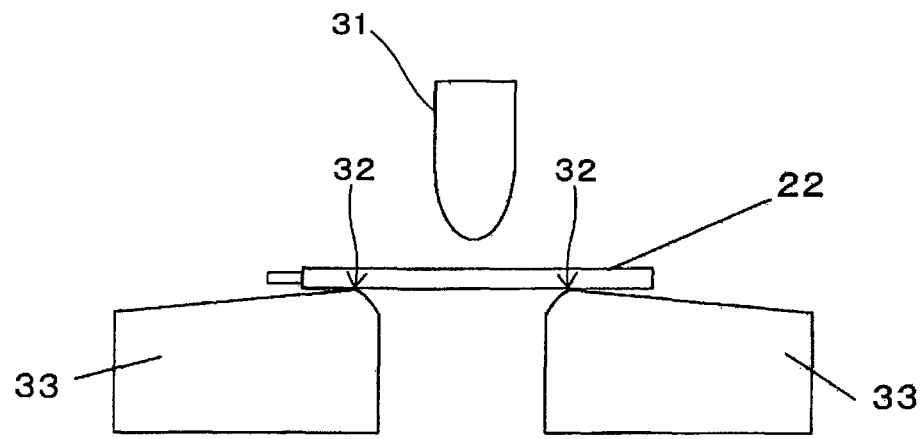
Figure 5:
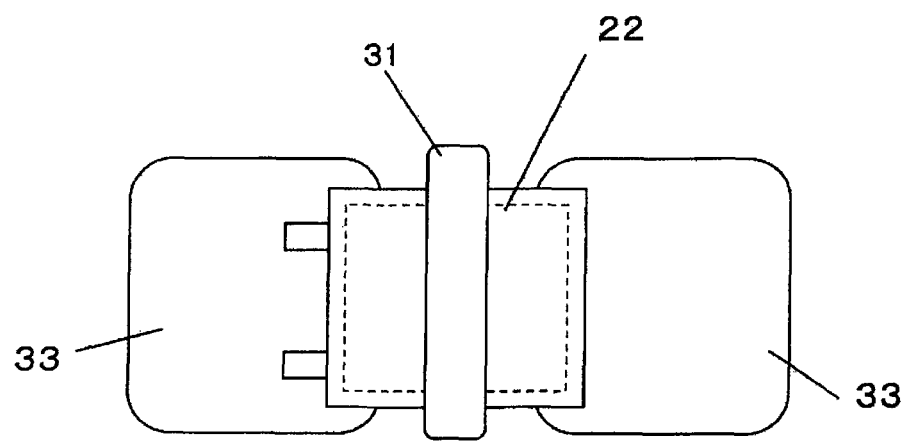

FIGS. 5(a) and 5(b) are a front view and a top view, respectively, for explaining how to perform a three-point bending test. A description is given here with the thin battery 22 taken as a test subject. The three-point bending test is performed as follows. First, the thin battery 22 is placed on a pair of base blocks 33. Each base block 33 has a support point 32 for supporting the thin battery 22. Then, an indenter 31 is moved downward to apply load to the thin battery 22 at the center between the two support points 32. Here, the measurement conditions for the three-point bending test were set such that the distance between the support points 32 was 30 mm, the radius of curvature of the tip end surface of the indenter 31 was 5 mm, the radius of curvature of the curved surface constituting the support point 32 was 2 mm, and the load application rate was 100 mm/min. In the case where an electrode group or a thin battery is taken as a test subject, the electrode group or the thin battery is placed on the base blocks 33 such that the load of the indenter 31 is applied thereto from the second electrode side.

5. Evaluation of Discharge Performance

The thin batteries (batteries Nos. 11, 111 and 112) according to the first Example, and the first and second Comparative Examples were subjected to a discharge test, to determine a discharge capacity of each thin battery. The conditions for the discharge test were set such that the ambient temperature was 25° C., the discharge current density (current value per unit area of the positive electrode) was 250 μA/cm$^2$, and the discharge cut-off voltage was 1.8 V.

6. Evaluation of Flex-Resistance Reliability

Figure 6:
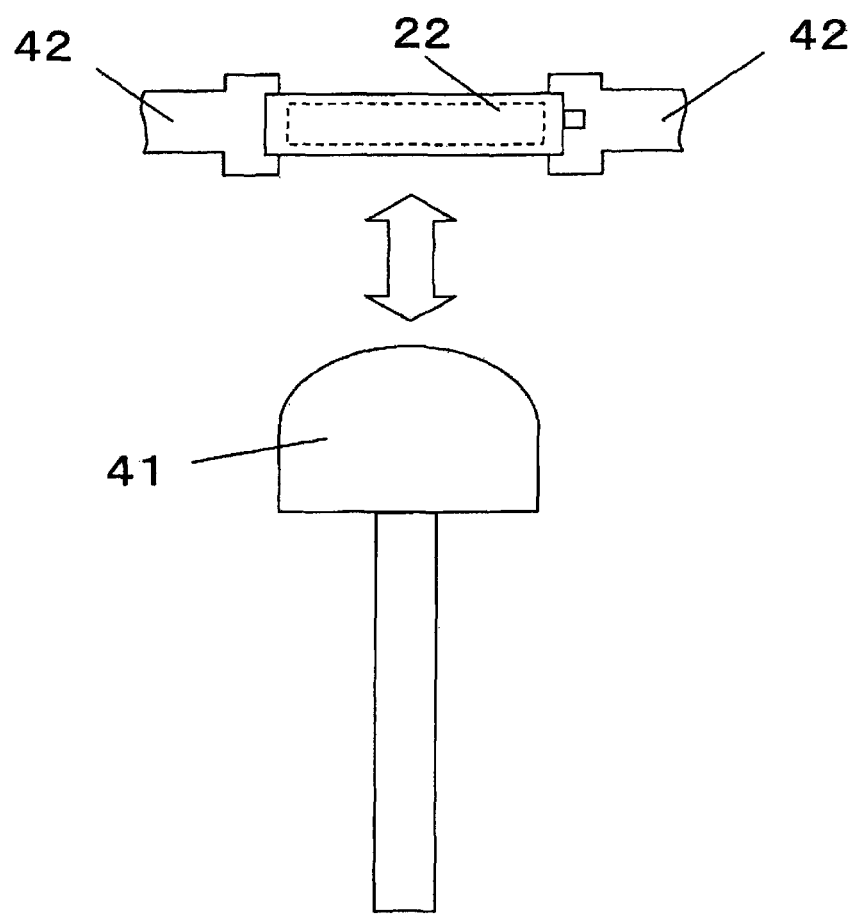

The thin batteries (batteries Nos. 11, 111 and 112) according to the first Example, and the first and second Comparative Examples were evaluated for their flex-resistance reliability. FIG. 6 is an illustration for explaining how to perform a flex resistance test for evaluation of flex-resistance reliability. A description is given here with the thin battery 22 taken as a test subject. The flex resistance test is performed as follows. First, the thin battery 22 is fixed by clamping the both thermally-fused and bonded end portions thereof between a pair of fixtures 42. Then, a jig 41 whose tip end surface has a radius of curvature of 20 mm is forced onto the thin battery 22 from the second electrode side, to allow the thin battery 22 to elastically deform along the tip end surface of the jig 41. Next, the jig 41 is moved away from the thin battery 22, to restore the original shape of the thin battery 22 before the elastic deformation.

The thin batteries according to the first Example, and the first and second Comparative Examples were subjected to the elastic deformation and restoration 10,000 times in total (the duration per one elastic deformation-restoration was approximately 30 seconds). The thin batteries after the flex resistance test were subjected to the discharge test under the same conditions as those described in "5. Evaluation of discharge performance", to determine a discharge capacity of each thin battery. The capacity retention rate (%) after the flex resistance test was calculated from the formula: (Discharge capacity after flex resistance test/Discharge capacity before flex resistance test)×100.

7. Evaluation Results of First Example, and First and Second Comparative Examples The evaluation results on the flexibility of the electrode groups Nos. 1, 101 and 102 are shown in Table 1. The evaluation results on the flexibility, discharge performance, and flex-resistance reliability of the batteries Nos. 11, 111 and 112 are shown in Table 2.

TABLE 1

| Electrode group No. | First electrode | | Second electrode | | Electrode group |
| | Polarity | Flexural modulus (MPa) | Polarity | Flexural modulus (MPa) | Flexural modulus (MPa) |
|---|---|---|---|---|---|
| 1 | Positive | 1500 | Negative | 550 | 200 |
| 101 | Negative | 550 | Positive | 1500 | 1000 |
| 102 | Positive | 1400 | Negative | 500 | 800 |

TABLE 2

| Battery No. | Flexibility Flexural modulus (MPa) | Discharge performance Discharge capacity (mAh) | Flex-resistance reliability Capacity retention rate (%) |
|---|---|---|---|
| 11 | 90 | 230 | 99 |
| 111 | 410 | 230 | 65 |
| 112 | 370 | 220 | 72 |

As shown in Table 1, in the electrode groups Nos. 1 and 102, the flexural modulus of the second electrode 12 was lower than that of the first electrode 11. In the electrode group No. 101, the flexural modulus of the second electrode 12 was higher than that of the first electrode 11. As for the flexural moduluses of the electrode groups Nos. 1, 101 and 102, the flexural moduluses of the electrode groups No. 1 and 102 were lower than that of the electrode group No. 101. This comparison shows that by setting the flexural modulus of the second electrode 12 lower than that of the first electrode 11, the flexural modulus of the electrode group as a whole is reduced.

As for the flexural moduluses of the electrode groups Nos. 1 and 102, the flexural modulus of the electrode group No. 1 was lower than that of the electrode group No. 102. This comparison shows that by laminating the second electrodes 12 with low flexural modulus on both surface of the first electrode 11, the flexural modulus of the electrode group as a whole is significantly reduced.

The foregoing evaluation results show the following. That is, as mentioned above, when the electrode group is bent, the upper and lower surfaces of the electrode group are stretched and compressed greatly. The stretch and compression at the center portion of the electrode group in its thickness direction, however, is small (see FIG. 10). Therefore, by arranging the first electrode 11 with high flexural modulus (i.e., low flexibility) at the center portion where the stretch and compression is small, and arranging the second electrode 12 with low flexural modulus (i.e., high flexibility) at each of the upper and lower portions where the stretch and compression is great, the flexural modulus of the electrode group as a whole is reduced (the flexibility is improved).

As for the flexibilities of the batteries Nos. 11, 111 and 112 in Table 2, the flexibility of the battery No. 11 was much higher than those of the batteries Nos. 111 and 112. This was because the battery No. 11 included the electrode group No. 1, and the flexibility of the battery group No. 1 was much higher than those of the battery groups Nos. 101 and 102. It is presumed that since high flexibility was achieved in the battery No. 1, the stress generated in the battery No. 1 was small when it was bent, and as a result, the flex-resistance reliability of the battery No. 1 was improved.

8. Second Example

In the second Example, the electrode group 21 and the thin battery 22 were produced in the same manner as in the first Example, except that the thickness of the positive electrode active material layer and the thickness of the negative electrode active material layer in the second Example were changed from those in the first Examples. Specifically, four electrode groups (electrode groups Nos. 2 to 5) differing in the thickness of the active material layers, and the thin batteries 22 (batteries Nos. 12 to 15) including these electrode groups were produced. The flexibility, discharge performance, and flex-resistance reliability thereof were evaluated in the same manner as described above.

9. Evaluation Results of Second Example

The evaluation results on the flexibility of the electrode groups Nos. 1 to 5 are shown in Table 3. The evaluation results on the flexibility, discharge performance, and flex-resistance reliability of the battery Nos. 11 to 15 are shown in Table 4.

TABLE 3

| | First electrode | | Second electrode | | Electrode group | |
| Electrode group No. | Thickness of active material layer (μm) | Flexural modulus (MPa) | Thickness of active material layer (μm) | Flexural modulus (MPa) | Thickness (μm) | Flexural modulus (MPa) |
|---|---|---|---|---|---|---|
| 1 | 90 | 1500 | 20 | 550 | 350 | 200 |
| 2 | 5 | 97 | 2 | 19 | 40 | 80 |
| 3 | 40 | 1000 | 15 | 200 | 230 | 120 |
| 4 | 130 | 2000 | 46 | 650 | 470 | 190 |
| 5 | 150 | 3000 | 53 | 800 | 530 | 380 |

TABLE 4

| Battery No. | Flexibility Flexural modulus (MPa) | Discharge performance Discharge capacity (mAh) | Flex-resistance reliability Capacity retention rate (%) |
|---|---|---|---|
| 11 | 90 | 230 | 99 |
| 12 | 50 | 110 | 99 |
| 13 | 70 | 170 | 99 |
| 14 | 90 | 280 | 95 |
| 15 | 190 | 290 | 75 |

The results in Table 3 show that when the flexural modulus of the first electrode 11 is 2000 MPa or less and the flexural modulus of the second electrode 12 is 650 MPa or less, the electrode group 21 has an improved flexibility (electrode groups Nos. 1 to 4).

The results in Table 4 show that the batteries Nos. 11 to 14 are excellent in flexibility. This is because the batteries Nos. 11 to 14 include the electrode groups Nos. 1 to 4, respectively, and the electrode groups Nos. 1 to 4 are excellent in flexibility. It is presumed that since high flexibility was achieved in the batteries Nos. 1 to 4, the stress generated in the batteries Nos. 1 to 4 was small when they were bent, and as a result, the flex-resistance reliability of the batteries Nos. 1 to 4 was improved.

As shown in Table 3, in the electrode group No. 2, the flexural modulus of the first electrode 11 was less than 100 MPa, and that of the second electrode 12 was less than 20 MPa. The results in Table 4 show that in the battery No. 12 including the electrode group No. 2, the electrode capacity was reduced. This indicates that, in the electrode group 21, the flexural modulus of the first electrode 11 is preferably 100 MPa or more, and the flexural modulus of the second electrode 12 is preferably 20 MPa or more.

10. Third Example

In the third Example, the electrode group 21 (electrode group No. 6) and the thin battery 22 (battery No. 16) were produced in the same manner as in the first Example, except that an alloy of Li and 3% Al (by mass) was used as the negative electrode active material in the third Example. The flexibility, discharge performance, and flex-resistance reliability thereof were evaluated in the same manner as described above.

11. Fourth Example

In the fourth Example, the electrode group 21 (electrode group No. 7) and the thin battery 22 (battery No. 17) were produced in the same manner as in the first Example, except that in the fourth Example, graphite having a volumetric mean particle size of 20 μm was used as the negative electrode active material, and $LiNi_{0.82}Co_{0.15}Al_{0.03}O_2$ (hereinafter denoted as "LNCA") having a volumetric mean particle size of 10 μm was used as the positive electrode active material. The flexibility, discharge performance, and flex-resistance reliability thereof were evaluated in the same manner as described above.

In this Example, the second electrode 12 (negative electrode) was produced as follows. A slurry was prepared using water as a dispersion medium such that the slurry contained the negative electrode active material, styrene-butadiene rubber, and carboxymethyl cellulose in a ratio of 98:1:1 (by mass). The slurry was applied onto an electrolytic copper foil, and dried, and then, the electrolytic copper foil was rolled. The negative electrode active material layer was thus formed on the surface of the electrolytic copper foil. The thickness of the negative electrode active material layer was 60 μm.

12. Evaluation Results of Third and Fourth Examples

The evaluation results on the flexibility of the electrode groups Nos. 1, 6 and 7 are shown in Table 5. The evaluation results on the flexibility, discharge performance, and flex-resistance reliability of the battery Nos. 11, 16 and 17 are shown in Table 6.

TABLE 5

| Electrode group No. | First electrode | | Second electrode | | Electrode group | |
|---|---|---|---|---|---|---|
| | Active material | Flexural modulus (MPa) | Active material | Flexural modulus (MPa) | Thickness (μm) | Flexural modulus (MPa) |
| 1 | $MnO_2$ | 1500 | Li | 550 | 350 | 200 |
| 6 | $MnO_2$ | 1500 | Li—Al alloy | 600 | 350 | 250 |
| 7 | LNCA | 1350 | C | 600 | 350 | 290 |

TABLE 6

| Battery No. | Flexibility Flexural modulus (MPa) | Discharge performance Discharge capacity (mAh) | Flex-resistance reliability Capacity retention rate (%) |
|---|---|---|---|
| 11 | 90 | 230 | 99 |
| 16 | 110 | 230 | 99 |
| 17 | 110 | 220 | 99 |

The results in Table 5 show that the electrode groups Nos. 6 and 7, like the electrode group No. 1, are excellent in flexibility. The batteries Nos. 16 and 17, like the battery No. 11, are excellent in flexibility, discharge performance, and flex-resistance reliability. In the secondary battery also, the results similar to those obtained in the primary battery can be obtained.

13. Examples of Electronic Device

Next, examples of an electronic device in which the thin battery 22 is to be incorporated are described. Specifically, such an electronic device includes an electronic device main body with flexibility, and the thin battery 22 is incorporated in the electronic device main body.

(A) Biological Information Measuring Device

Figure 7:
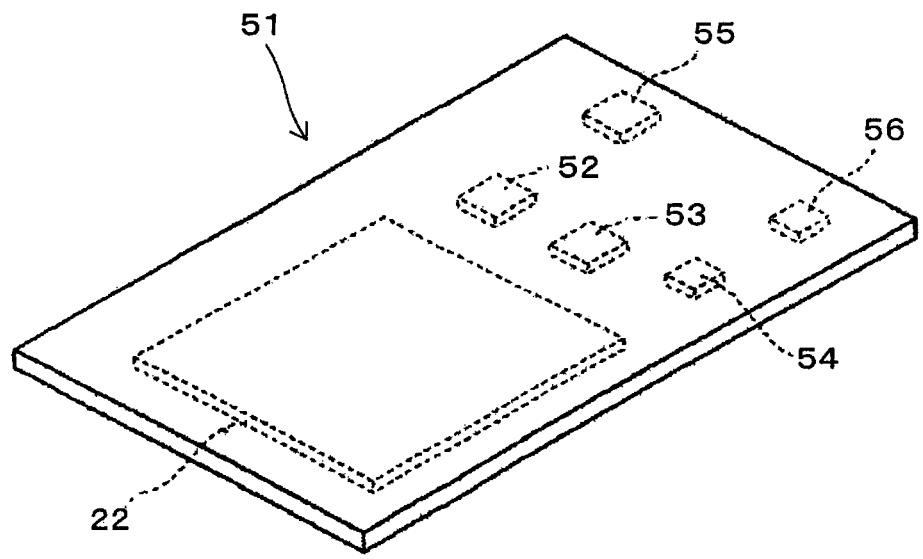

FIG. 7 is an oblique view illustrating a biological information measuring device as an example of the electronic device. The biological information measuring device is a device that acquires biological information, such as blood pressure, body temperature, and pulse, and wirelessly transmits the acquired information to a facility such as a hospital. The biological information measuring device is a portable device that operates in contact with the skin of human body.

As illustrated in FIG. 7, a biological information measuring device 51 includes a temperature sensor 51, a pressure sensor 53, an information transmission element 54, a GPS sensor 55, and a control element 56 including a predetermined control circuit. While the biological information measuring device 51 is kept in contact with the skin of human body, the temperature sensor 52 measures body temperature, and the pressure sensor 53 measures blood pressure. The GPS sensor 55 acquires information on the location of the biological information measuring device 51 (location information). The control element 56 includes a circuit for controlling the acquisition time and the transmission time of the biological information, and furthermore, the time when power is to be supplied to the biological information measuring device 51. The information transmission element 54 wirelessly sends the biological information to a processor such as a computer equipped with a receiver.

As described above, the thin battery 22 is excellent in flexibility. As such, even when the thin battery 22 is incorporated in the biological information measuring device 51, the tin battery 22 does not impair the flexibility of the biological information measuring device 51. Therefore, the person who uses the biological information measuring device 51 is unlikely to feel discomfort even when the biological information measuring device 51 is kept in close contact with the skin for a long period of time.

(B) Iontophoresis-Type Transdermal Administration Device

Figure 8:
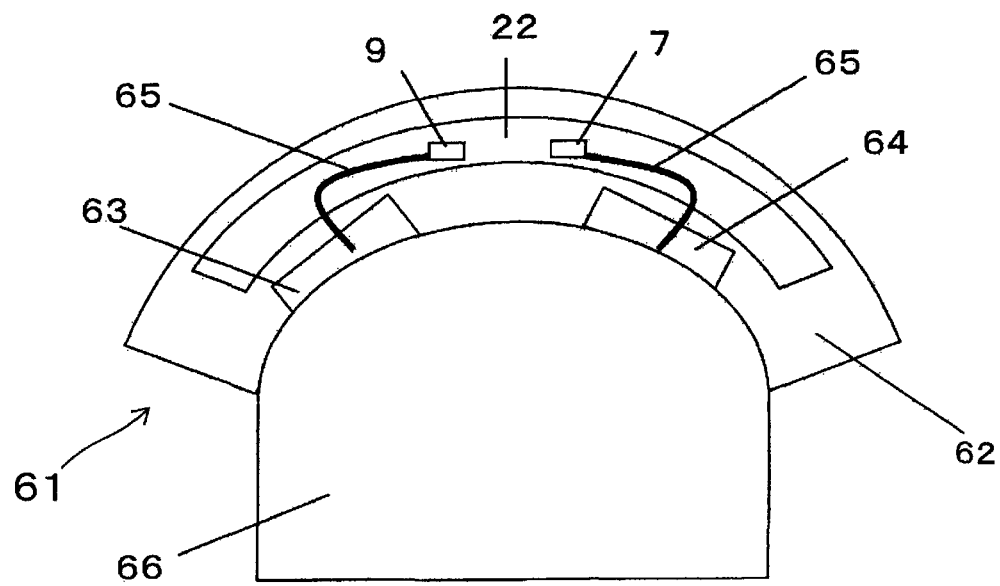
Figure 9:
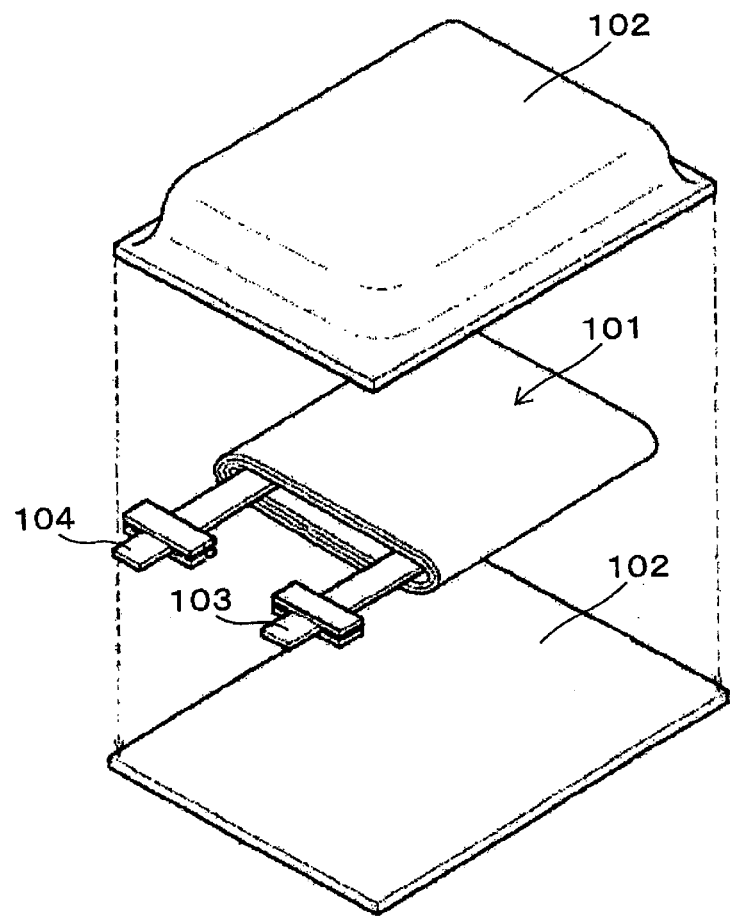

FIG. 8 is a cross-sectional view illustrating an iontophoresis-type transdermal administration device as another example of the electronic device. The iontophoresis-type transdermal administration device is a device that promotes permeation of ionic medication through the human membrane, by utilizing electric energy. The iontophoresis-type transdermal administration device is a portable device that operates in contact with the skin of human body.

As illustrated in FIG. 8, an iontophoresis-type transdermal administration device 61 includes an elastic sheet 62, and the thin battery 22 is bent and embedded inside the elastic sheet 62. As described above, the thin battery 22 is excellent in flexibility. As such, the thin battery 22 can be embedded in a bent state inside the elastic sheet 62 as illustrated in FIG. 8. The iontophoresis-type transdermal administration device 61 further includes a cathode chamber 63 and an anode chamber 64. The cathode chamber 63 and the anode chamber 64 are electrically connected via a wiring 65 to an electrode lead 9 (negative electrode lead) and an electrode lead 7 (positive electrode lead) of the thin battery 22, respectively. In the case where the ionic medication to be supplied to the human body is a positively-charged cation, the ionic medication is sealed in the anode chamber 64. The anode chamber 64 then serves as a donor electrode chamber, and the cathode chamber 63 serves as a counter electrode chamber. Conversely, in the case where the ionic medication to be supplied to the human body is a negatively-charged anion, the ionic medication is sealed in the cathode chamber 63. The cathode chamber 63 then serves as a donor electrode chamber, and the anode chamber 64 serves as a counter electrode chamber.

As illustrated in FIG. 8, the iontophoresis-type transdermal administration device 61 when used is stuck to a human body 66. The thin battery 22 applies voltage across the cathode chamber 63 and the anode chamber 64. This allows the ionic medication to move from the donor electrode chamber to the skin of the human body 66. On the other hand, an endogenous ion having a polarity opposite to that of the ionic medication is extracted from the skin into the counter electrode chamber. In short, the iontophoresis-type transdermal administration device 61 and the human body 66 form an electric circuit, and ion exchange occurs between the iontophoresis-type transdermal administration device 61 and the human body 66.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

INDUSTRIAL APPLICABILITY

The thin battery of the present invention can be mounted in various electronic devices without being limited to the biological information measuring device and the iontophoresis-type transdermal administration device. The thin battery of the present invention is particularly useful when mounted in electronic devices with flexibility, specifically, in electronic devices that require the battery incorporated therein to be highly flexible.

REFERENCE SIGNS LIST

1 Electrode current collector
2 Electrode active material layer
3 Electrode current collector
4 Electrode active material layer
5 Electrolyte layer
6 Protruding portion
7 Electrode lead
8 Protruding portion
9 Electrode lead
11 First electrode
12 Second electrode
13 Housing
21 Electrode group
22 Thin battery
31 Indenter
32 Support point
33 Base block
41 Jig
42 Fixture
51 Biological information measuring device
52 Temperature sensor
53 Pressure sensor
54 Information transmission element
55 GPS sensor
56 Control element
61 Iontophoresis-type transdermal administration device
62 Elastic sheet
63 Cathode chamber
64 Anode chamber
65 Wiring
66 Human body
101 Electrode group
102 Housing
103 Positive electrode lead
104 Negative electrode lead

The invention claimed is:

1. An electrode group for thin batteries comprising:
   a sheet-like first electrode;
   a sheet-like second electrode disposed over each of both surfaces of the first electrode, and having a polarity opposite to a polarity of the first electrode; and
   an electrolyte layer interposed between the first electrode and the second electrode,
   the second electrode having a flexural modulus lower than a flexural modulus of the first electrode.

2. The electrode group for thin batteries according to claim 1, wherein a thickness of the electrode group is 700 μm or less, the flexural modulus of the first electrode is 100 MPa or more and 2000 MPa or less, and the flexural modulus of the second electrode is 20 MPa or more and 650 MPa or less.

3. The electrode group for thin batteries according to claim 1, wherein the first electrode is a positive electrode, and the second electrode is a negative electrode.

4. The electrode group for thin batteries according to claim 3, wherein:
   the first electrode has a positive electrode current collector, and a positive electrode active material layer formed on each of both surfaces of the positive electrode current collector, the positive electrode active material layer including manganese dioxide;
   the second electrode has a negative electrode current collector, and a negative electrode active material layer formed on one surface of the negative electrode current collector, the negative electrode active material layer including lithium or a lithium alloy; and
   the second electrode is disposed over each of both surfaces of the first electrode such that the negative electrode active material layer faces the positive electrode active material layer.

5. The electrode group for thin batteries according to claim 1, wherein the flexural modulus of the first electrode is 100 MPa or more and 2000 MPa or less, and the flexural modulus of the second electrode is 20 MPa or more and 650 MPa or less.

6. A thin battery comprising an electrode group, and a pouch-like housing accommodating the electrode group,
   the electrode group comprising:
   a sheet-like first electrode;
   a sheet-like second electrode disposed over each of both surfaces of the first electrode, and having a polarity opposite to a polarity of the first electrode; and
   an electrolyte layer interposed between the first electrode and the second electrode,
   the second electrode having a flexural modulus lower than a flexural modulus of the first electrode, and
   a sum of a thickness of the electrode group and a thickness of the housing being 1.0 mm or less.

7. The thin battery according to claim 6, wherein a thickness of the electrode group is 700 μm or less, the flexural modulus of the first electrode is 100 MPa or more and 2000 MPa or less, and the flexural modulus of the second electrode is 20 MPa or more and 650 MPa or less.

8. The thin battery according to claim 6, wherein the flexural modulus of the first electrode is 100 MPa or more and 2000 MPa or less, and the flexural modulus of the second electrode is 20 MPa or more and 650 MPa or less.

9. An electronic device comprising an electronic device main body with flexibility, and a thin battery incorporated in the electronic device main body,
   the thin battery comprising an electrode group, and a pouch-like housing accommodating the electrode group, and
   the electrode group comprising:
   a sheet-like first electrode;
   a sheet-like second electrode disposed over each of both surfaces of the first electrode, and having a polarity opposite to a polarity of the first electrode; and
   an electrolyte layer interposed between the first electrode and the second electrode,
   the second electrode having a flexural modulus lower than a flexural modulus of the first electrode.

10. The electronic device according to claim 9, wherein the electronic device main body is a device that operates in contact with the skin of a human body.

11. The electronic device according to claim 9, wherein a thickness of the electrode group is 700 μm or less, the flexural modulus of the first electrode is 100 MPa or more and 2000 MPa or less, and the flexural modulus of the second electrode is 20 MPa or more and 650 MPa or less.

12. The electronic device according to claim 9, wherein the flexural modulus of the first electrode is 100 MPa or more and 2000 MPa or less, and the flexural modulus of the second electrode is 20 MPa or more and 650 MPa or less.

* * * * *